United States Patent [19]

Törnblom

[11] Patent Number: 4,819,181

[45] Date of Patent: Apr. 4, 1989

[54] PERFORMANCE INCREASING SIGNAL PROCESSING DEVICE

[75] Inventor: Bengt H. Törnblom, Västerås, Sweden

[73] Assignee: Tornbloms Kvalitetskontroll AB, Sweden

[21] Appl. No.: 38,764

[22] Filed: Apr. 15, 1987

[30] Foreign Application Priority Data

Apr. 18, 1986 [SE] Sweden ................................. 8601785

[51] Int. Cl.⁴ ..................... G01N 27/82; G01N 27/90
[52] U.S. Cl. .................................... 364/507; 364/552; 324/237; 324/240
[58] Field of Search ................ 364/507, 552; 324/234, 324/225, 262, 415, 238, 237, 240; 73/634

[56] References Cited

U.S. PATENT DOCUMENTS

| | | | |
|---|---|---|---|
| 3,268,805 | 8/1966 | Normando | 324/240 |
| 3,471,685 | 10/1969 | Bishop, III | 364/552 |
| 3,898,469 | 8/1975 | Nichols et al. | 356/430 |
| 4,075,498 | 2/1978 | Takasura et al. | 250/562 |
| 4,213,183 | 7/1980 | Barron et al. | 364/552 |
| 4,555,664 | 11/1985 | Davis et al. | 324/225 |
| 4,583,181 | 4/1986 | Gerber et al. | 364/507 |
| 4,584,529 | 4/1986 | Aoyama | 324/234 |
| 4,628,261 | 12/1986 | Hüschelrath | 364/507 |
| 4,642,786 | 2/1987 | Hansen | 364/559 |
| 4,755,753 | 7/1988 | Chern | 324/237 |
| 4,761,610 | 8/1988 | Svegander et al. | 324/227 |

FOREIGN PATENT DOCUMENTS 0046182 12/1980 Japan ................................. 324/237

Primary Examiner—Parshotam S. Lall
Assistant Examiner—Ellis B. Ramirez
Attorney, Agent, or Firm—Watson Cole Grindle & Watson

[57] ABSTRACT

A testing device for storing and/or processing of fault signals obtained from at least one transducer with associated electronic equipment, which fault signals are at least partially derived from one or more features, for example a defect on a test object, such as a steel blank. The fault signals are supplied to at least one discriminating circuit to distinguish between relevant and trivial fault signals. The relevant signals are then supplied to a plurality of different signal processing circuits which, for example, operate in parallel but independently.

7 Claims, 2 Drawing Sheets

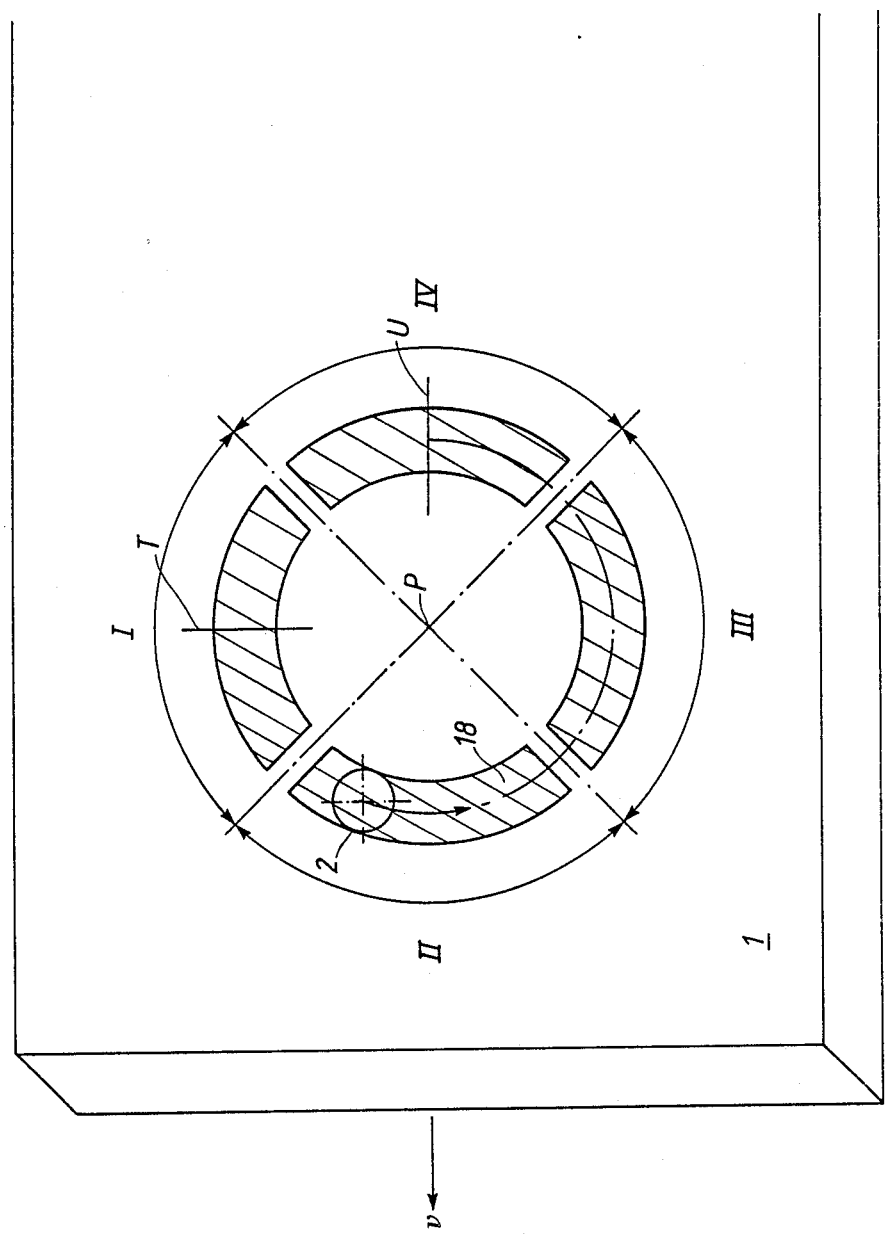

PERFORMANCE INCREASING SIGNAL PROCESSING DEVICE

TECHNICAL FIELD

The present invention relates to a device for processing signals obtained from at least one transducer, which is movable in relation to a test object, with associated electronic equipment, which signals at least partially originate from one or more features, for example a defect in or on the test object, the device comprising at least one discriminating circuit, at least one selector, and at least two signal processing circuits.

DISCUSSION OF PRIOR ART

Within the field of non-destructive testing and measurement, the use of eddy current field testing seems to be moving towards increasingly higher signal processing rates. The reason for this is that the performance requirements with regard to surface scanning are being successively increased, so that nowadays it is desired, for example, to be able to indicate the position of a small surface crack on a test object with an accuracy within a few centimeters, as well as to indicate rapidly the size and nature of the crack.

In, for example, crack detection carried out on hot continuously cast billets, the billet surface is therefore scanned by mean of, for example, an eddy current transducer which often rotates at a speed of several thousands of revolutions per minute in a path with a radius of, for example, 100 mm.

The large billet surface in combination with the surface scanning pattern of the transducer per unit of time results in the amount of signal information requiring processing becoming very large and unwieldy in those cases where it is desired to study in detail the fault signals and their positions, i.e. the nature of the fault and its address on the billets.

The prior art method when attempting to master the problems mentioned above is to try and store the fault signal information (e.g. by means of simple run registers) until the subsequent signal processing, for example in a computer, has caught up and is able to process the stored information.

The above-mentioned method, however, involves the risk that, for example in the case of many defects on a billet surface, fault signal information will be lost because of, for example, "overflow" of storage memories due to a long cycle time in the computers used. The risk of indiscriminate loss of signal information is a considerable and often unacceptable shortcoming of prior art testing devices.

SUMMARY OF THE INVENTION

One object of the present invention is to provide a testing device in which the transducer is able to scan the test object in an operating mode which permits small defects and their positions to be detected without indiscriminate loss of signal-information. The ability to detect small defects presupposes a very fine-meshed scanning pattern for at least one transducer, which, in those cases where it is desired to operate with a limited number of transducers, means that each transducer, for example a rotary surface transducer, has to rotate at high speed. Especially in those cases where, for example for reasons of cost, only one transducer is available, the transducer arrangement has to be moved rapidly back and forth over the billet by way of some type of transducer manipulator, for example an industrial robot, in order to be able to scan the billet surface successively when casting is in progress. The requirement for a high number of turns of rotation is then, of course, greatly increased. This, in turn, places very high demands on the subsequent signal treatment, including the signal processing, which has to take place very rapidly so that no defects are undetected and thus missed or even inadequately mapped.

The present invention aims to provide a solution to the problems mentioned above and other problems associated therewith. A device according to the invention is characterized in that at least one transducer is adapted to rotate in a closed path, in that at least one discriminating circuit is adapted to be used for separating signals of a minor interest, and in that the remaining relevant signals which are of interest for the case in question, such as signals which are detrimental to a continuous casting process, for example crack signals, are automatically distributed to the signal processing circuits, operating in parallel but independently, these relevant signals being adapted to be provided with address information about which part of the test object they refer to.

The invention can be regarded as a capacity increasing signal processing device, based on a combination of discrimination between fault signals, so that those which fulfill certain conditions are retained, and parallel signal processing of the retained signals occurs.

By limiting the number of signal processing fault signals in this way as well as by processing the signals in parallel-operating circuits (or function blocks), the signal processing capacity of a testing device can be considerably increased with improved, or at least retained, reliability.

The invention has particular utility in the field of crack detection based on so-called eddy current techniques, and can then be regarded as a complement to the subject-matter of Törnblom's U.S. patent Application Nos. 621,916 abandoned in favor of continuation application Ser. No. 926,850, filed Nov. 3, 1986, 680,258, now U.S. Pat. No. 4,646,013, 699,594 now U.S. Pat. No. 4,661,777, 702,314 now U.S. Pat. No. 4,703,265, 816,270 now U.S. Pat. No. 4,734,642 filed respectively on June 15, 1984, Nov. 13, 1984, Feb. 8, 1985, Feb. 15, 1985 and Jan. 6, 1986.

In this specification the following terms have the meanings ascribed to them below:

By test object is meant, for example, a continuously cast billet, sheet metal, steel melt, wire, rod and tube.

By defect is meant, for example, a crack, a surface defect, a rolled-in flake, a surface depression, a deep-seated defect, a foreign body inclusion, a void or bubble and a mis-shapen region of the test object.

By transducer is meant, for example, a surface-sensing eddy current transducer and a coil supplied with several carrier frequencies, By transducer arrangement is meant the means for sweeping the transducer relative to the test object, for example, a device which moves a transducer coil in a circular path over the surface of the test object.

By fault signal is meant the signal which at least partially originates from a defect in or on the test object.

By defect variable is meant, for example, a type of defect, the depth of a crack and the position of a defect on the test object.

BRIEF DESCRIPTION OF THE DRAWINGS

The invention will now be described in greater detail, by way of example, with reference to the accompanying drawings, wherein FIG. 2 shows part of the sweep path of the transducer of the device of FIG. 1 divided into four quadrants.

DESCRIPTION OF PREFERRED EMBODIMENTS

Figure 1:
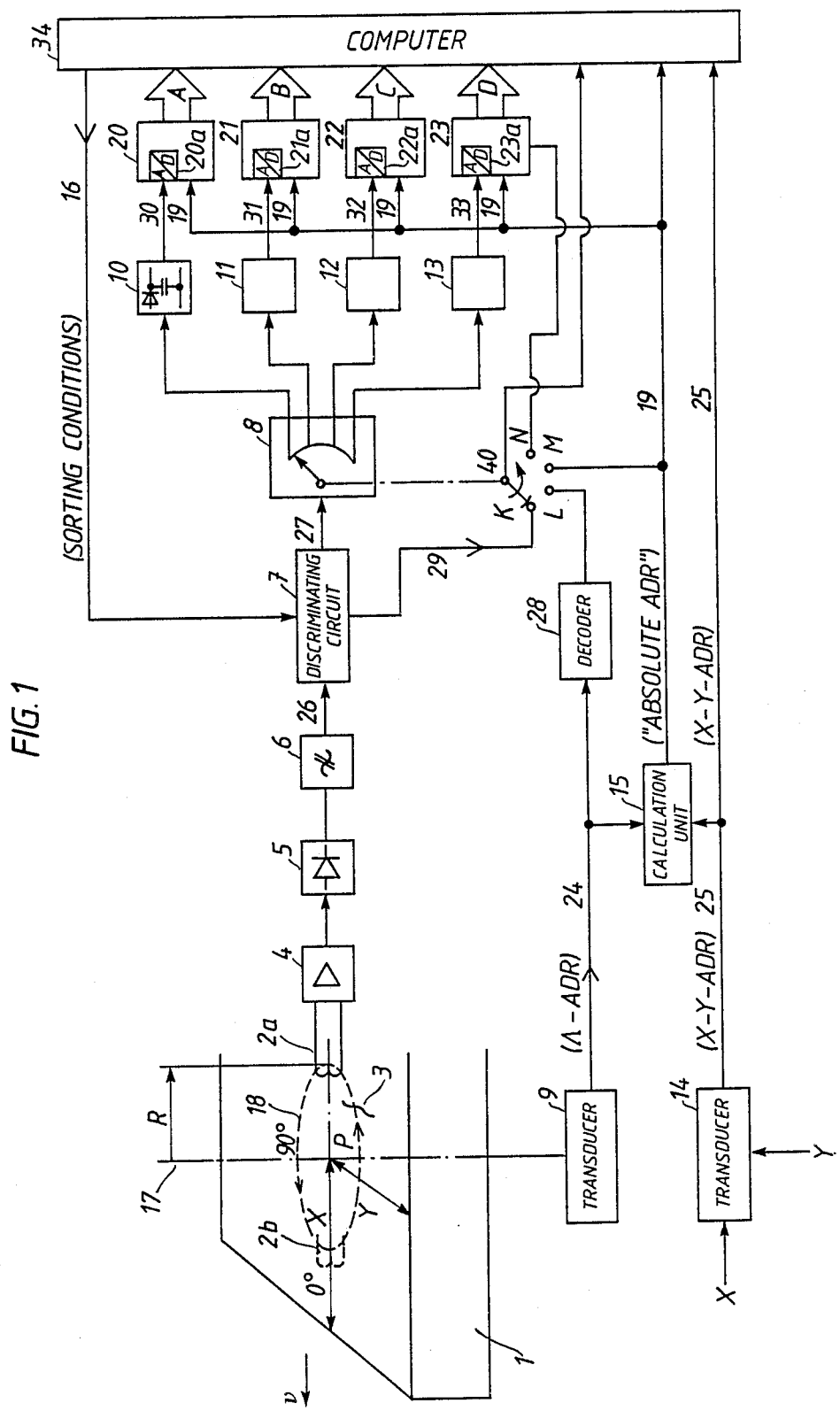
FIG. 1 shows in schematic form the principle behind the working of a device according to the invention.

The invention can be described as follows, which is to be regarded as one of many feasible variants of the device according to the invention.

FIG. 1 shows a continuously cast billet 1 moving at a rate of v m/min. An eddy current-based surface transducer 2 rotates over the surface of the billet 1 along a circular path 18 of radius R, parallel to the surface. At least one crack or other defect 3 is assumed to be present in the surface. FIG. 1 shows the transducer 2 at two different positions (2a and 2b, respectively). The center axis 17 of the path of rotation 18 is largely perpendicular to the surface of the billet 1 and located at the distances X and Y, respectively, from two mutually perpendicular edges of the billet 1, and it can be moved with the of, for example a transducer manipulator mechanism (not shown), whereby the distances X and Y are, of course, changed.

The distances X and Y represent the coordinate address of the transducer arrangement, whereas, for example, the position of the transducer 2 in relation to the center point P can be regarded as a transducer rotation address superimposed on the coordinate address of the transducer arrangement.

Taken together, the above-noted addresses constitute the so-called absolute address of the transducer 2, which refers to a precise point on the billet surface.

The coordinate address 25 of the transducer arrangement is obtained from a position transducer 14, whereas the transducer rotation address 24 is obtained from a position transducer 9 consisting of, for example, an angle transducer mounted on the center shaft of the transducer arrangement. In a calculation unit 15, the absolute address 19 is calculated from the signals 24 and 25.

The transducer 2 is connected to an amplifier circuit 4, a detector unit 5 and a filter 6. The output signal 26 from the filter 6 contains a great deal of signal information which is derived, for example, from the surface of the test object, such as signals which define features of each defect 3 passed by he transducer 2 during rotation. At high speeds of rotation and rapid movement of the transducer arrangement, i.e. advance of the point P over the billet surface, the amount of information in the signal 26 often increases to an unmanageable level.

When the test object, i.e. in this example the billet 1, is not the end product but is intended to be further processed in, for example, a strip mill or the like, some types of defect can be ignored since they will not affect the subsequent process. For this reason it is possible, via a discriminating circuit 7 in FIG. 1 which includes one or more condition functions, to eliminate out those signals which can be associated with a relatively harmless defect and which therefore are of no interest so far as further signal processing and position determination are concerned. Examples of such harmless defects may be minor surface irregularities (i.e. oscillation marks), the presence of small flakes, etc. Another case where some defects can be ignored is where spot grinding of the test object is to be carried out. In that case it is sufficient to locate the deepest defect, for example the crack on the partial area in question, e.g. a surface quadrant, and to set the grinding machine so that the deepest defect is removed.

Within the scope of the invention, the discriminating circuit 7 can be positioned at other locations in the system, for example it can be included as part of each of the parallel channels shortly to be described. The fundamental effect will, however, be the same. In similar manner, other functional blocks can be varied in position within the circuit without departing from the scope of the invention.

The discriminating circuit 7 is controlled by sorting conditions circuit 16, which can be varied and could be based on, for example, the fault properties which are expected to result from the alloy in the test object in question. The sorting conditions 16 may, for example, be based on:

signal frequency
signal amplitude
frequency spectrum
pulse density and
signal appearance, etc.

The result of the separation which takes place in the discriminating circuit 7 is the generation of a number of selected fault signals 27. These signals are supplied to a selector 8 which is ganged to rotate with a switch 40. The selector 8 and switch 40 are shown as four-position devices in FIG. 1 but more or less than four-positions could be employed.

In the first position of selector 8 the output 27 of the discriminator circuit 7 is fed to a first intermediate memory 10, in the second position to a second memory 11 and so on. In the first position (K) of the switch 40 the output of the discriminator circuit 7 is fed via a line 29 to a computer 34. The signals on the line 29 can provide information about, for example, in which quadrant the transducer 2 is momentarily situated. In the second position (L) of the switch 40 the output of a decoder 28 is fed to the computer 34. The input signal to the decoder 28, consists of the angle code 24 from the position transducer 9. In this way, the selector 8 will distribute the signals 27 to the four parallel signal storing intermediate memories 10, 11, 12 and 13, which will thus store signals which are each derived from a different part of the transducer rotation path, for example one quadrant thereof.

The signals 30, 31, 32 and 33 which output from the memories 10 to 13 thus represent stored selected signals from, in this case, a respective transducer rotation quadrant.

In certain cases, it is sufficient to process these signals further, for example by means of the subsequently positioned computer 34, possibly together with the XY-address information 25. In those cases where the requirements for processing speed are high, it is often advantageous to supplement the signals 30, 31, 32 and 33 by address information 19 and this addition of signal information takes place in signal processing circuits 20, 21, 22 and 23.

The signal outputs A, B, C and D from the processing circuits 20 to 23 can therefore contain, not only the sorted-out signals that represent "significant" faults but also information about the precise locations or addresses on the billet 1 from which these "significant" fault signals emanate.

From FIG. 1 it is clear that the selector 8 can be controlled in several different ways depending on the choice of the position of the switch 40. In the position of the switch 40 shown in FIG. 1, i.e. position (K), the selector 8 is controlled by a transducer variable, for example the type of crack or the level of crack depth. In the second position (L) of switch 40, the selector 8 is controlled by the angular position of the transducer 2 around the path 18. In the third position (M) the selector 8 is controlled by the absolute address of the transducer 2 on the test object 1. In the fourth position (N) the selector 8 is controlled as a function of the memory status of the respective parallel channel, i.e. if there are free memories available in any channel. Which mode of control or condition to choose is dependent on how the final measurement result is intended to be used.

As an alternative to allowing the selector 8 to be controlled by the signal 24, i.e. the second position (L), the fault signals 27 can be distributed with the aid of the signal 19, i.e. the third position (M), whereby the distribution takes place, in principle, as a function of the position of the transducer 2 in relation to the test object 1. The number of parallel channels or outputs (A-D) should then be extended.

In this way it is relatively simple to allow the fault signals, which are acquired during different turns of the transducer rotation but which refer to the same point or area on the billet surface, to be stored together via, for example, an integration part, so that a mean signal value is obtained for the respective point or partial area on the billet 1. This increases the precision of the measurement.

The outputs A, B, C and D may, for example, be allowed to feed a respective memory which successively assumes a mean value referring to a suitably selected partial area on the billet surface.

This mean value generation may, of course, also take place in the blocks 20-23, if this is considered appropriate.

The most important condition for being able to carry out the mean value generation described here and other similar signal processing operations, where information is obtained on separate occasions but which refers to the same section of the surface, is that each defect is rapidly provided with unique address information.

To enable this to be carried out in a simple manner, rapid preferably hardware-generated address information and similarly rapid processing of the signals are required, the parallel intermediate signal storing with possibly associated signal processing forming an important part.

A consequence of this is also that the requirements on the subsequently positioned computer 34 are not so high, and therefore it is often possible to use conventional computers.

To be able to determine the position and orientation of a defect, a requirement is that the transducer rotates very rapidly, since in that way the amount of information will increase because, for example, the transducer is able to traverse the crack several times with different angles of intersection.

For the same reason, different types of fault can be determined and sorted and the orientation of the defects can be calculated if the number of turns of rotation is sufficiently high. The consequence of a high number of turns is that each fault signal is short, often with a duration of less than 1 ms, which means that it will be virtually impossible to signal process these signals directly via computers without the aid of supplementary hardward solutions. For this reason the intermediate memories 10, 11, 12 and 13 are used, consisting of analog memories containing a rectifier and a subsequent capacitor which is charged to the peak value of the fault signal via the rectifier.

However, there is nothing preventing the intermediate memories being manufactured to a digital design, if this is considered appropriate.

FIG. 2 shows how the transducer coil 2 and its path of rotation 18 over the billet 1 are positioned. In the case of eddy current testing, the sensitivity to defects, is normally greatest when the transducer crosses the crack transversely, i.e. at an angle of 90°. The sensitivity is normally greatly decreased when the transducer crosses the crack at an angle which is smaller than 45°. This results in the sensitivity to transverse cracks (T) being greatest in quadrants I and III and in the sensitivity to longitudinal cracks (U) being greatest in quadrants II and IV, provided the quadrants are oriented as shown in FIG. 2. This is one of the reasons why it may be advantageous to choose the second position of the selector 8 (i.e. position (L) in switch 40) when it is desired to separate transverse and longitudinal cracks.

The signal processing circuits 20, 21, 22 and 23 may contain analog-digital convertors $20a$ to $23a$ which convert the analog signals from the capacitors in the memories 10-13 to digital signals.

Through the parallel signal processing circuits, these A/D convertors $20a$ to $23a$ will have time to carry out the signal conversion.

The signal processing circuits may also, for example, include one microcomputer each for additional sophisticated, parallel signal processing.

The microcomputers may also be included as part of a "hand-shaking procedure" with the superordinate computer 34, as well as act as a run register while waiting for the superordinate computer 34 to be ready to receive the fault signals in question.

If it is assumed that the speed of rotation of the transducer is 3000 r.p.m., i.e. 50 r.p.s., the time taken for one complete revolution will be 1000/50=20 ms.

If sorting condition 16 is to select the largest fault signal per quadrant, the signal outputs A, B, C and D will show the measured value in question during a period of $>\frac{3}{4}\cdot 20$ ms, i.e. >15 ms. The subsequent computer 34 thus has >15 ms in which to process the signals/information on the outputs A to D. Per output this will then be >15/4, i.e. >3.75 ms, which is a simple task compared with the pulse duration of the fault signal which is about 0.1-0.5 ms.

If it is desired to operate with one computer per output, this will of course be even more favourable, since in that case each computer will have >15 ms in which to process the information in question.

Often it is not only of interest to locate the most deep-seated defect but it is also desired to obtain an overall broad outline picture of the quality of billet surface. A suitable way of getting access to the information required for this is to calculate a so-called "quality code" as a function of the number of fault signals/defects per chosen unit of surface, for example in one quadrant, and/or the size and/or orientation and/or type of these defects.

The quality code may, for example, be indicated as a number referring to the quality of the whole billet surface or parts thereof.

Because of the high capacity of signal processing, made possible by the invention, and the resultant accurate addressing possibility of the defects in question, the computer 34 is able to reproduce the billet surface or a part thereof via a display member such as, for example, a VDU or a printer (not shown).

This reproduction may be according to scale and may, for example, be divided into equally large squares, representing 200×200 mm large squares on the billet surface.

In the respective square of such a reproduction, the greatest crack depth, for example, could then be indicated by a numerical code or the like.

This information is thereafter used, for example, by a billet grinding operator when the defects are to be ground away, thereby resulting in optimum use of the grinding machine.

The corresponding information in the computer can, of course, also be used for automatic control of equipment for removing defects which are detrimental to a subsequent process.

The invention can be realized using both hardware and software. In order to utilize the invention in full, however, hardware solutions for, for example, the intermediate memories 10–13 are primarily used.

The invention can be varied in many ways within the scope of the following claims.

What is claimed is:

1. A device for processing fault signals obtained from at least one transducer movable in a closed path in relation to the surface of a test object, said signals being at least partially derived from at least one defect in said surface, comprising:
    means for determining at least two different conditions of said at least one surface defect from said fault signals;
    means for determining the angular position of said at least one transducer with respect to said surface in a plane substantially parallel thereto;
    means for determining the position of said at least one transducer with respect to a given coordinate system associated with said surface;
    means for calculating an absolute address of said at least one transducer with respect to said surface;
    means for storing said at least two conditions;
    means for distributing said at least two conditions to said means for storing;
    means for processing at least one of said at least two conditions in accordance with at least one of said absolute address, said angular position and said position; and
    means for switching selected ones of said at least one of said two different conditions, said absolute address, said angular position and said position to said means for processing.

2. A device according to claim 1, wherein said means for processing calculates said address with respect to a given fault signal as a function of the position address and said angular position.

3. A device according to claim 1, wherein said closed path is divided into a number of parts, and said at least one of said at least two different fault conditions is processed by said processing means with respect to a selected one of said parts.

4. A device according to claim 3, wherein said at least one of said at least two different fault conditions is also processed by said processing means with respect to the angular rotation of said at least one transducer.

5. A device according to claim 2, wherein said at least one transducer includes a position transducer for providing said position.

6. A device according to claim 1, wherein said distributing means distributes said at least two conditions in accordance with the available memory capacity of said storing means.

7. A device according to claim 1, wherein fault signals originating from different rotational movements of said at least one transducer and having the same address are processed together by said means for processing to obtain a statistical means value of said at least one fault condition.

* * * * *